(12) United States Patent
Brugger et al.

(10) Patent No.: US 7,776,219 B2
(45) Date of Patent: Aug. 17, 2010

(54) METHODS, DEVICES, AND SYSTEMS FOR HEMODILUTION

(75) Inventors: James M. Brugger, Newburyport, MA (US); Jeffrey H. Burbank, Boxford, MA (US); Martin Stillig, Dransfeld (DE)

(73) Assignee: NxStage Medical, Inc., Lawrence, MA (US)

( * ) Notice: Subject to any disclaimer, the term of this patent is extended or adjusted under 35 U.S.C. 154(b) by 30 days.

(21) Appl. No.: 12/015,420

(22) Filed: Jan. 16, 2008

(65) Prior Publication Data

US 2008/0177215 A1 Jul. 24, 2008

Related U.S. Application Data

(62) Division of application No. 10/774,127, filed on Feb. 6, 2004, now abandoned, which is a division of application No. 09/904,709, filed on Jul. 12, 2001, now abandoned.

(51) Int. Cl.
*B01D 61/00* (2006.01)
*B01D 61/14* (2006.01)
*B01D 61/24* (2006.01)
*B01D 61/28* (2006.01)
*A61M 1/18* (2006.01)
*A61M 1/34* (2006.01)

(52) U.S. Cl. ............... 210/651; 210/321.6; 210/321.72; 210/321.8; 210/456; 210/493.2; 210/646; 210/650

(58) Field of Classification Search ............... 210/321.6, 210/321.72, 321.78, 321.8, 456, 321.76, 210/321.87, 321.88, 321.89, 493.2, 645, 210/646, 650, 651
See application file for complete search history.

(56) References Cited

U.S. PATENT DOCUMENTS

| | | | |
|---|---|---|---|
| 4,047,563 A | 9/1977 | Kurata | |
| 4,201,673 A | 5/1980 | Kanno et al. | |
| 4,784,768 A | 11/1988 | Mathieu | |
| 4,828,543 A * | 5/1989 | Weiss et al. | 604/6.09 |
| 4,975,247 A | 12/1990 | Badolato et al. | |
| 5,084,244 A * | 1/1992 | Muramoto | 422/46 |
| 5,236,586 A | 8/1993 | Antoni et al. | |
| 5,352,361 A | 10/1994 | Prasad et al. | |
| 5,480,552 A | 1/1996 | Soltys et al. | |
| 5,762,869 A | 6/1998 | White et al. | |
| 5,820,767 A | 10/1998 | Kane et al. | |

(Continued)

FOREIGN PATENT DOCUMENTS

JP  4-231670 A  8/1992

(Continued)

*Primary Examiner*—John Kim
(74) *Attorney, Agent, or Firm*—Mark A. Catan; Miles & Stockbridge P.C.

(57) ABSTRACT

Devices, methods, and system that prevent clotting of blood during blood-processing procedures such as hemofiltration, hemodialysis, and hemodiafiltration are described. A filter with a cap has a housing that is shaped to receive a blood filter. The housing has an inlet for blood and may have an outlet for waste and ultrafiltrate. The cap is attached to the housing. The cap has an outlet for blood and a port adjacent the outlet for receiving dilution fluid. Methods of use during blood-processing procedures to provide immediate hemodilution to blood exiting entering and/or exiting a filter are also described.

11 Claims, 7 Drawing Sheets

U.S. PATENT DOCUMENTS

| | | | |
|---|---|---|---|
| 5,882,516 | A | 3/1999 | Gross et al. |
| 5,916,647 | A | 6/1999 | Weinstein |
| 6,050,278 | A | 4/2000 | Arnal et al. |
| 6,074,559 | A | 6/2000 | Hahmann et al. |
| 6,303,036 | B1 | 10/2001 | Collins et al. |
| 6,315,895 | B1 | 11/2001 | Summerton et al. |
| 6,406,631 | B1 | 6/2002 | Collins et al. |
| 6,582,385 | B2 | 6/2003 | Burbank et al. |
| 6,702,561 | B2 | 3/2004 | Stillig et al. |
| 6,776,912 | B2 * | 8/2004 | Baurmeister ................ 210/646 |
| 6,918,886 | B1 | 7/2005 | Baurmeister |
| 6,966,979 | B2 | 11/2005 | Pedrazzi et al. |
| 7,285,106 | B2 | 10/2007 | Collins et al. |
| 7,410,582 | B2 | 8/2008 | Bernard et al. |
| 2002/0053540 | A1 | 5/2002 | Collins et al. |
| 2003/0010718 | A1 | 1/2003 | Burbank et al. |
| 2003/0215356 | A1 * | 11/2003 | Patterson et al. .............. 422/45 |
| 2004/0127842 | A1 | 7/2004 | Collins et al. |
| 2005/0000882 | A1 | 1/2005 | Brugger et al. |
| 2007/0163943 | A1 | 7/2007 | Collins et al. |
| 2008/0197062 | A1 | 8/2008 | Collins et al. |

FOREIGN PATENT DOCUMENTS

| | | |
|---|---|---|
| WO | 00/53293 A1 | 9/2000 |
| WO | WO 2005/061026 A3 | 7/2005 |

* cited by examiner

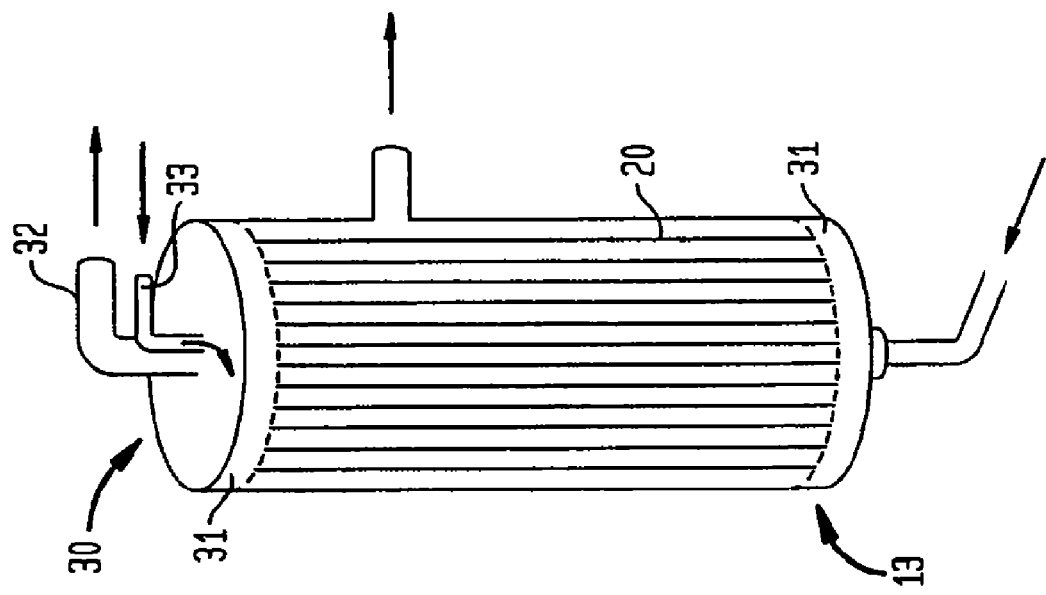
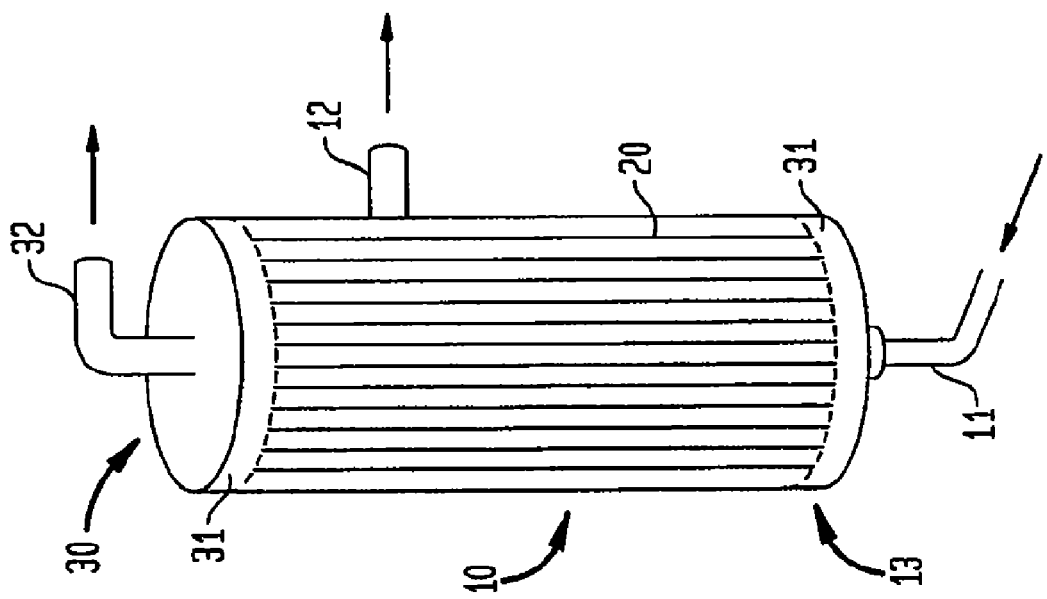

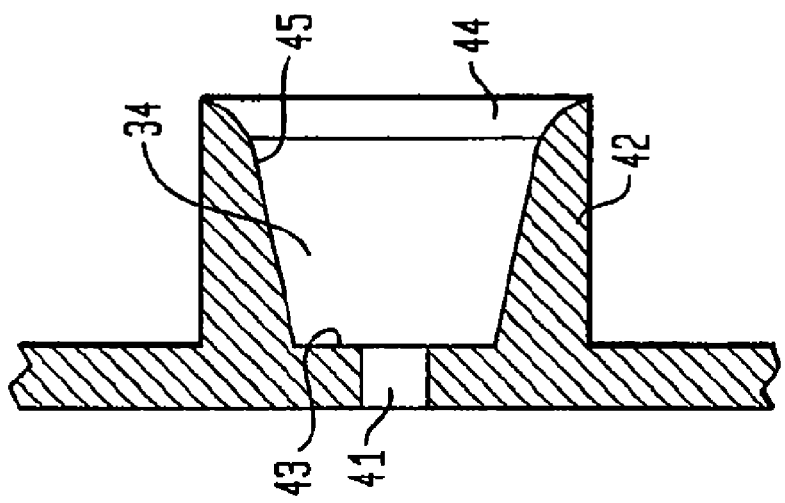
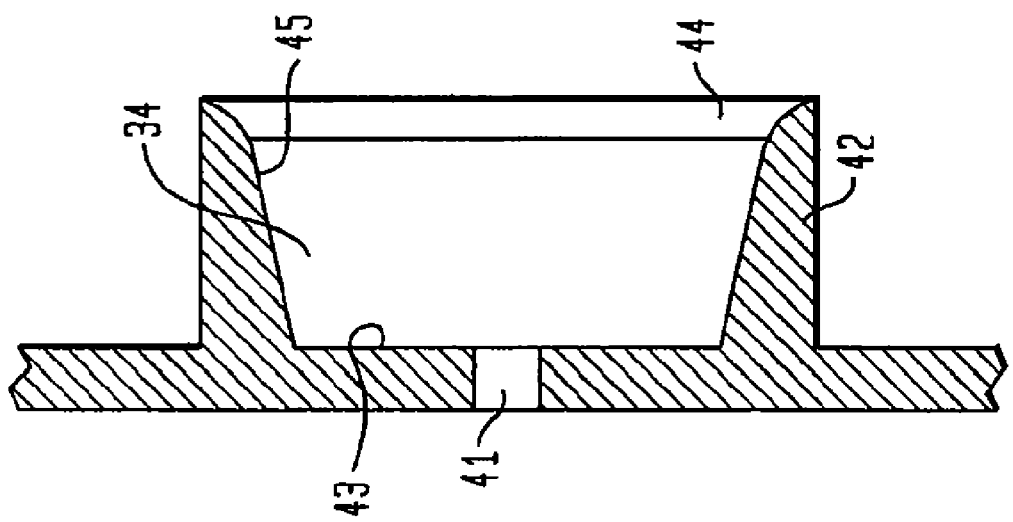

METHODS, DEVICES, AND SYSTEMS FOR HEMODILUTION

CROSS REFERENCE TO RELATED APPLICATIONS

This application is a divisional of U.S. Ser. No. 10/774,127, filed Feb. 6, 2004, now abandoned, which is a divisional of U.S. Ser. No. 09/904,709, filed on Jul. 12, 2001, now abandoned, the contents of which are incorporated herein by reference in their entireties.

FIELD OF THE INVENTION

The present invention relates generally to devices and methods useful in preventing coagulation in filtered blood during hemofiltration. More specifically, the devices and methods provide a cap having a port, the cap adapted for attachment to a blood filter housing to provide hemodilution of blood as it enters and/or exits the filter.

BACKGROUND OF THE INVENTION

Undesired coagulation of blood often complicates blood-processing procedures such as hemofiltration, hemodialysis, and hemodiafiltration, particularly where a filter is used. Blood generally coagulates by transforming soluble fibrinogen into insoluble fibrin by activation of numerous circulating proteins that interact in a cascading series of limited proteolytic reactions. At each step of reaction, a clotting factor undergoes limited proteolysis and becomes an active protease that in turn activates the next clotting factor until finally a solid fibrin clot is formed. Fibrinogen (factor I) is activated by thrombin (factor IIa), which is converted from prothrombin by activated factor X. There are two separate coagulation pathways that activate factor X—the intrinsic system and the extrinsic system. Activation of the extrinsic system requires tissue thromboplastin (factor III), which is released from damaged tissue into the circulating blood to activate clotting. The intrinsic system, on the other hand, has all the factors necessary for coagulation contained in the circulating blood. The intrinsic system is, for example, partially responsible for clotting of blood in a test tube. Aggregation of platelets caused by stagnation of blood also facilitates blood coagulation.

During hemofiltration, for example, blood is removed from the patient, filtered through a filtering column to remove waste products, and returned to the patient's circulation. However, during removal of waste products, fluid is also removed, causing concentration of blood leaving the outflow tubing. As a result of hemoconcentration, hematocrit rises, and the intrinsic coagulation pathway and platelets are activated causing clotting of blood around the outlet of the filtering column, thereby compromising the hemofiltrating process.

What is needed are devices and methods that can be used with a filtering column during blood-processing procedures, such as hemofiltration, hemodialysis, hemodiafiltration, and peritoneal dialysis, to prevent clotting. Existing devices are inadequate for this purpose.

SUMMARY OF THE INVENTION

The present invention provides devices and methods that prevent clotting of blood during blood-processing procedures, such as hemofiltration, hemodialysis, and hemodiafiltration. More particularly, blood is diluted by replacement fluid, such as saline, Ringer's lactate, or other physiological solutions, as it enters and/or exits the filter. In a first embodiment, the device, also known as a filter, is comprised of a bundle of hollow fiber membrane made of resins such as polysulfone that is fixed in a cylindrical housing with a potting material. The interior of the fibers is the blood flow path. The exterior of the fibers is the dialysate and/or waste space. The potting material is typically a polyurethane material. The cylindrical housing may have one or two access ports. One port is for the hemofiltration filter, and two ports allow dialysate to flow through the housing contacting the exterior surface of the membrane for hemodialysis or hemodiafiltration. In one embodiment, the open fibers at the end of the cylindrical housing are covered at both ends with a cap. One cap is the blood entry cap, the other is the blood exit cap. In other embodiments, the housing includes end plates at one or both ends, the end plates integral with the housing.

The exit cap is attached to the housing, in some cases removably attached, and generally at a position opposite the inlet cap. The exit cap has an outlet for blood and a port adjacent the outlet for receiving replacement fluid. In certain embodiments, the blood outlet, the replacement fluid port, the blood inlet, and/or the waste outlet of the filter assembly communicate with bond sockets adapted to receive flexible tubing.

In another embodiment, the filter has an outlet or exit cap for blood at one end and an inlet or inlet cap at the other end, the cap having an inlet for blood and a port adjacent to the inlet for receiving dilution fluid, such as saline, Ringer's lactate, or other physiological solutions. The housing also includes access ports for waste and ultrafiltrate.

In still another embodiment, the housing includes first and second caps at opposite ends and an outlet for waste and ultrafiltrate. The first cap has an inlet for blood and a port adjacent to the inlet for receiving dilution fluid. The second cap has an outlet for blood and a port adjacent to the outlet for receiving dilution fluid.

In use, blood is passed through the blood inlet of the entry cap, through the filter membrane fibers, and through the blood outlet of the exit cap. Replacement fluid or dilution fluid, such as saline, Ringer's lactate, or other physiological solutions, is infused into the port adjacent the blood outlet to produce hemodilution at the blood outlet. Alternatively, the fluid is infused into the port adjacent the blood inlet of the entry cap to produce hemodilution at the inlet. In still another alternative method, fluid is infused into the port adjacent the blood inlet of the entry cap and into the port adjacent the blood outlet of the exit cap to produce hemodilution as blood enters and exits the filter housing. In certain constrictions the replacement fluid swirls in a circular pattern in a headspace that is defined by the gap between the filter and the cap. Swirling of the replacement fluid facilitates mixing of the fluid and the blood, thereby preventing hemoconcentration and stasis of blood, and sweeping any particles of thrombus away from the filter.

The advantages associated with the hemodilution cap described herein include (1) preventing coagulation during blood processing procedures, (2) manufacturing efficiency, i.e., reducing plastic used in disposable components, (3) eliminating up to two bonds and up to two components, (4) less expense in materials costs and manufacturing costs, (5)

more robust system, not subject to tolerances like bonding two rigid parts, and (6) integration of parts saves labor, materials, and precious resources.

BRIEF DESCRIPTION OF THE DRAWINGS

FIG. 1A depicts a filter within a housing for hemofiltration.

FIG. 1B depicts a filter within a housing having a replacement fluid port adjacent the blood outlet port for hemofiltration.

FIG. 4A depicts a fluid bond socket communicating with the blood outlet.

FIG. 4B depicts a fluid bond socket communicating with the replacement fluid port.

DETAILED DESCRIPTION

Figure 1D:
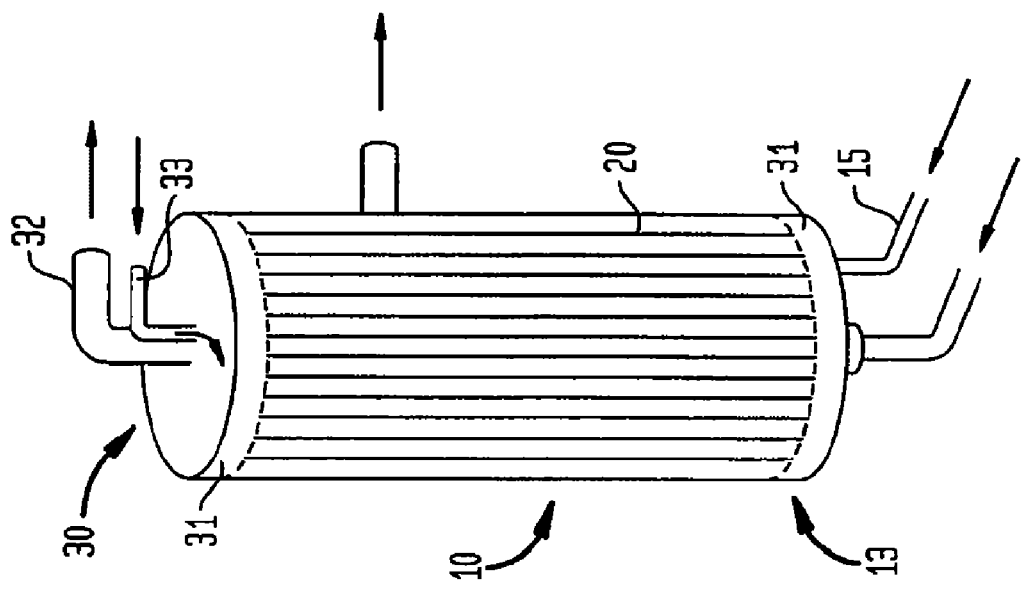
FIG. 1D depicts a filter within a housing having replacement fluid ports adjacent both the blood inlet port and the blood outlet port for hemofiltration.

During blood-processing procedures, such as hemofiltration, hemodialysis, and hemodiafiltration, blood has a tendency to clot as it passes through processing equipment, particularly where it exits the outlet of a filter, due to hemoconcentration. In FIG. 1A, the hemofiltration device includes cylindrical housing 10 which contains filter fibers 20 that remove waste from blood passing through the fibers. It will be understood that any other suitable shape can be used for the housing. Housing 10 is equipped with entry cap 13 having blood inlet 11. Waste and ultrafiltrate that are removed from the blood exits the housing through waste outlet 12. Exit cap 30 is mounted on housing 10 opposite blood entry cap 13. Headspace 31 is formed in the gap between filter fibers 20 and cap 30 and between filters 20 and cap 13. Headspace 31 communicates with blood outlet 32. Each of the inlet 11 waste outlet 12 and blood outlet 32 are adapted for attachment to flexible tubing sections that connect with a blood processing system.

In FIG. 1B, cap 30 further includes replacement fluid inlet port 33 that communicates with headspace 31. Replacement fluid is infused through port 33 to effect hemodilution of blood exiting filter 20. The system thereby reconstitutes blood as close as possible to the exit from the filter fibers. In this way hemodilution is accomplished with one part (cap 30) and two bonds (one between tubing and port 32, and another between tubing and port 33).

Figure 1C:
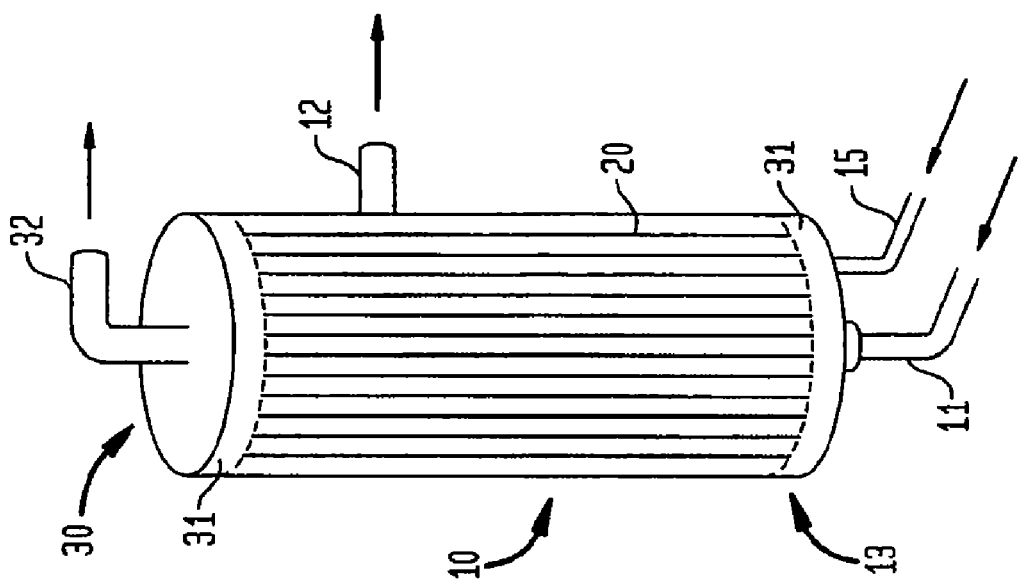
FIG. 1C depicts a filter within a housing having a replacement fluid port adjacent the blood inlet port for hemofiltration.

In FIG. 1C, housing 10 includes cap 13 having blood inlet 11 and dilution fluid inlet port 15 that communicates with headspace 31. Blood is diluted as it enters housing 10, thereby helping to prevent coagulation.

In FIG. 1D, housing 10 includes cap 13 having blood inlet and dilution fluid inlet port 15 that communicates with headspace 31. The housing also includes cap 30 having blood outlet 32 and fluid inlet port 33 that communicates with headspace 31. Dilution fluid is infused through port 33 and port 15 to effect hemodilution of blood entering and exiting filter 20.

Figure 1E:
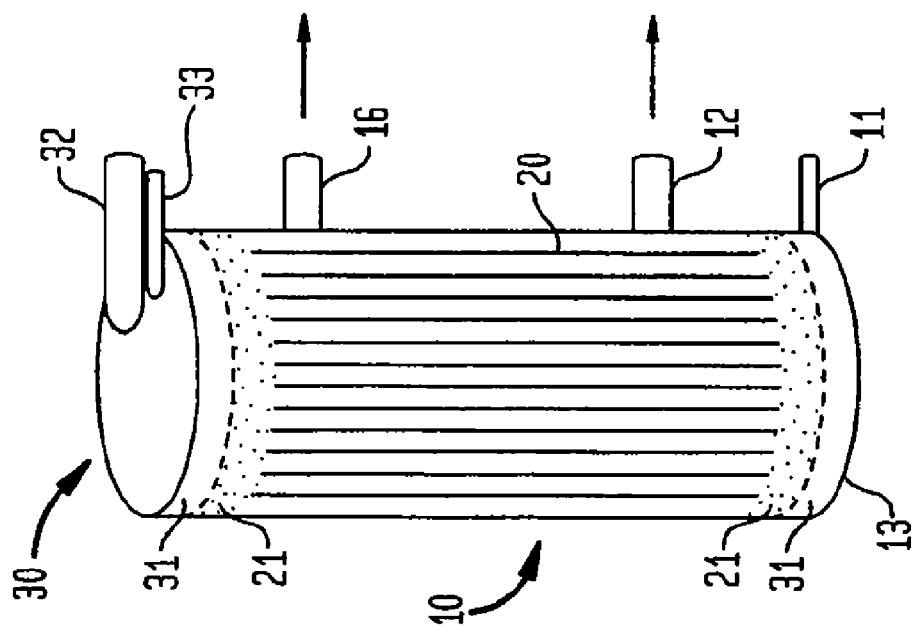
FIG. 1E depicts a filter within a housing for hemodiafiltration having dialysate inlet and outlet ports.
Figure 1F:
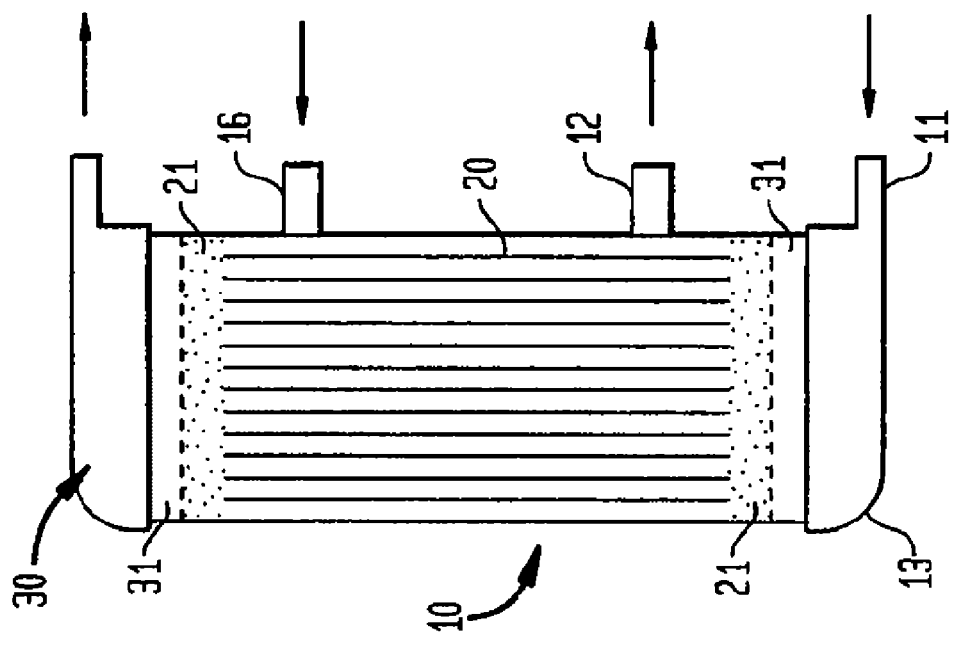
FIG. 1F depicts a filter within a housing for hemodiafiltration having a replacement fluid port adjacent the blood outlet port.

FIG. 1E shows a housing 10 designed for hemodiafiltration. Housing 10 includes dialysate inlet 16 and dialysate outlet 12 to establish countercurrent dialysate flow. Filter fiber membrane 20 is mounted within potting material 21 at both ends, where the potting material typically is a polyurethane material. In FIG. 1F, cap 30 further includes replacement fluid inlet port 33 that communicates with headspace 31. Replacement fluid is infused through port 33 to effect hemodilution of blood exiting filter 20 as described for other embodiments above. It will be understood that for hemodiafiltration, a hemodilution cap may be included alternatively on the inlet to effect pre-dilution of blood, and/or on both the inlet and outlet.

Figure 2:
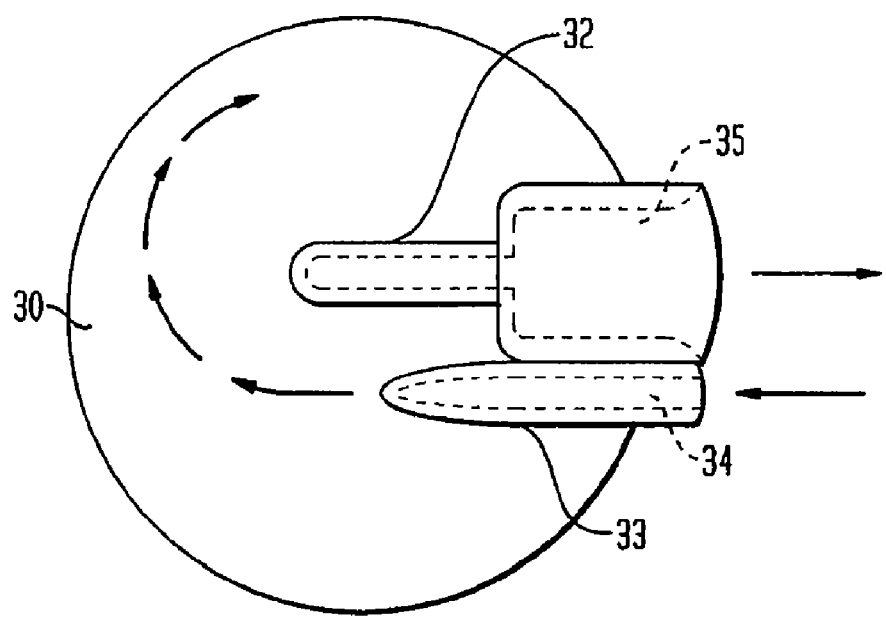
FIG. 2 depicts a filter-housing cap having a replacement fluid port adjacent the blood outlet port for hemofiltration.

FIG. 2 shows a top view of cap 30 having blood outlet 32 and replacement fluid infusion port 33. In use, replacement fluid, such as saline, Ringer's lactate, sterile filtered dialysate, or other physiological solutions, enters through port 33 and establishes a swirling current within headspace 31. This current has the beneficial effect of sweeping thrombus particles that may have accumulated in the headspace and flushing the particle through outlet 32. Inlet blood flow rate will typically be 50-1000 mL/min, preferably 350-600 mL/min. Infusion of dilution fluid at the exit cap will generally be 1-50% of inlet blood flow, preferably 20-30% in order to establish swirling. The foregoing ranges are set forth solely for the purpose of illustrating typical operating parameters. The actual parameters for operation of a device constructed according to the principles of the present invention may obviously vary outside of the listed ranges without departing from those basic principles.

Infusion port 33 includes bond socket 34, and outlet 32 includes bond socket 35. Each bond socket is adapted to receive flexible tubing. Where the tubing is generally constructed of PVC and the bond socket is constructed of any one of a number of thermoplastic resins including PVC, polycarbonate, ABS, etc., PVC being preferable as it is solvent bonded to the housing, the tubing may be fused to the bond socket by brief immersion in cyclohexanone or other suitable organic solvent before inserting the tubing in the bond socket. Soft PVC is flexible, allowing the cap to have an interference fit when solvent bonded. This makes it less susceptible to tolerance problems.

Figure 3A:
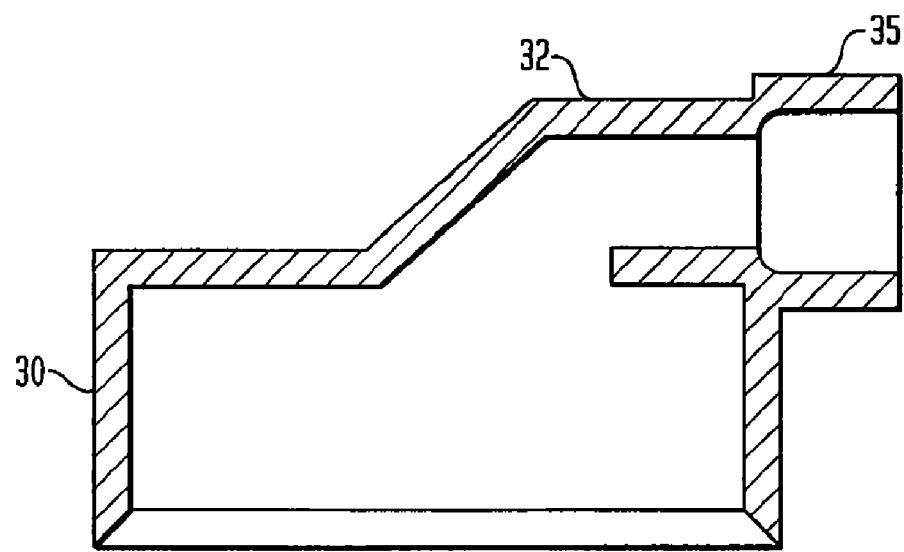
FIG. 3A depicts a cross-sectional view of a filter housing cap having a replacement fluid port adjacent the blood outlet port for hemofiltration.
Figure 3B:
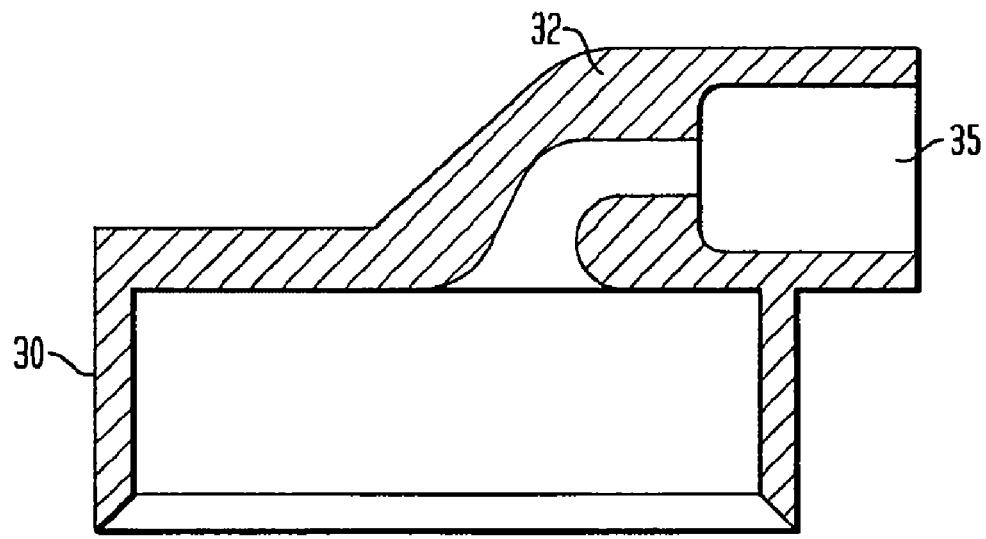
FIG. 3B depicts another cross-sectional view of a filter housing cap having a replacement fluid port adjacent the blood outlet port for hemofiltration.
Figure 3C:
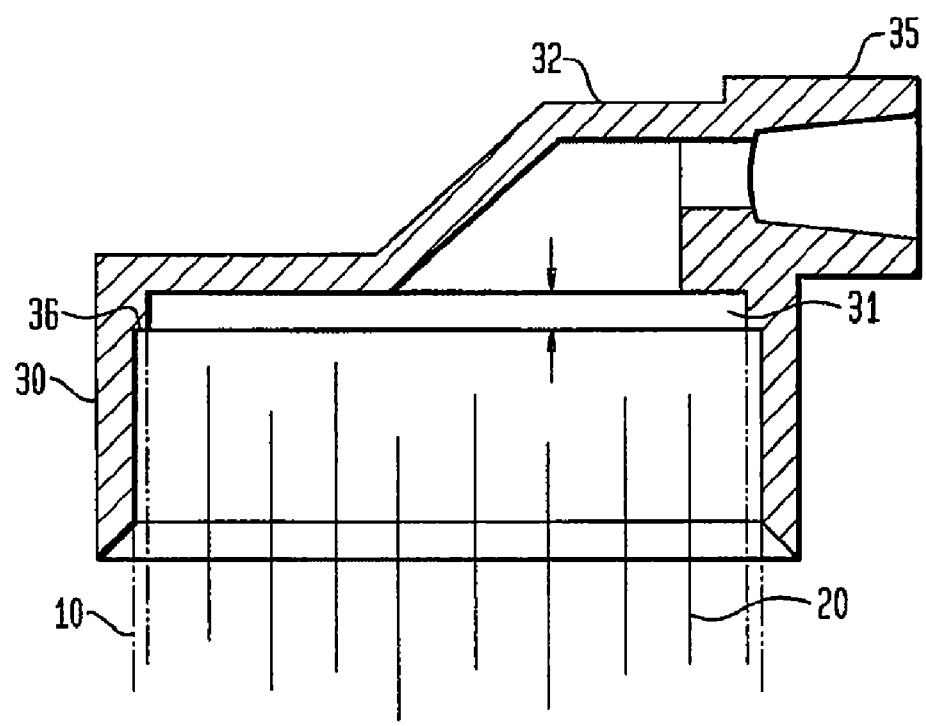
FIG. 3C depicts another cross-sectional view of a filter housing cap having a replacement fluid port adjacent the blood outlet port and a headspace for hemofiltration.

FIG. 3A depicts a side view of an embodiment of cap 30 with blood outlet 32 and bond socket 35. FIG. 3B depicts a side view of another embodiment of cap 30 having blood outlet 32 and bond socket 35. FIG. 3C depicts a side view of still another embodiment of cap 30 having blood outlet 32 and bond socket 35. Filter housing 10 is slideably received within the opening in cap 30 when fully inserted, housing 10 rests against annular ridge 36. Headspace 31 is defined by the gap between filter 20 and cap 30.

FIG. 4A shows the details of bond socket 35 communicating with the blood outlet designed for interference fit with appropriately sized tubing. Passage 41 has a dimension of approximately 0.185 inches in diameter. Surface 43 is approximately 0.248 inches in diameter. Annular member 42 has a height of approximately 0.35 inches. Surface 45 is approximately 0.252 inches in diameter. Thus, blood outlet 32 communicates with a quarter inch bond socket. Replacement fluid infusion port 33 communicates with bond socket 34 shown in details in FIG. 4B. Passage 41 has a dimension of approximately 0.098 inches in diameter. Surface 43 is approximately 0.142 inches in diameter. Annular member 42 has a height of approximately 0.31 inches. Surface 45 is approximately 0.147 inches in diameter. The foregoing ranges are set forth solely for the purpose of illustrating typical device dimensions. The actual dimensions of a device constructed according to the principles of the present invention may obviously vary outside of the listed ranges without departing from those basic principles.

Figure 5:
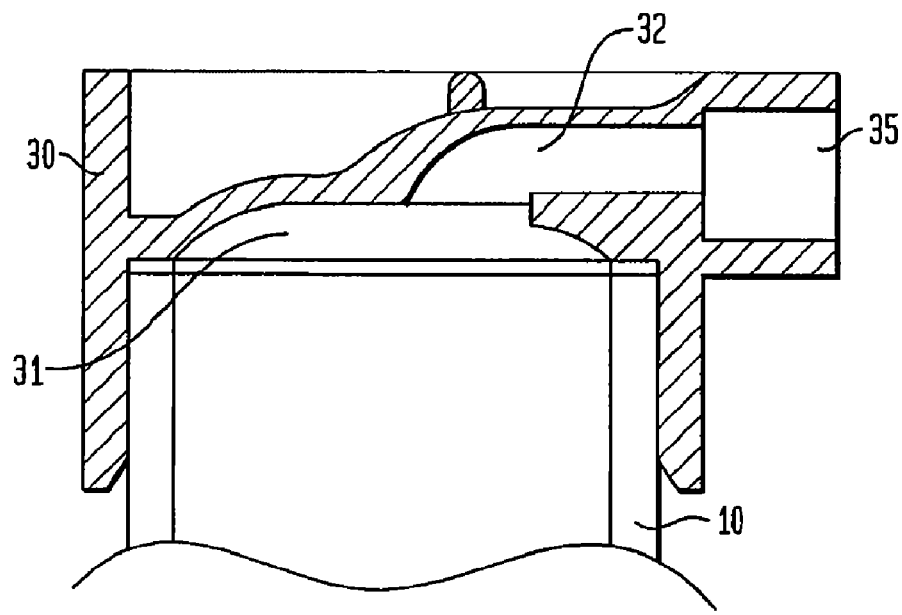
FIG. 5 depicts a filter-housing cap removably mounted on a filter housing for hemofiltration.
Figure 6:
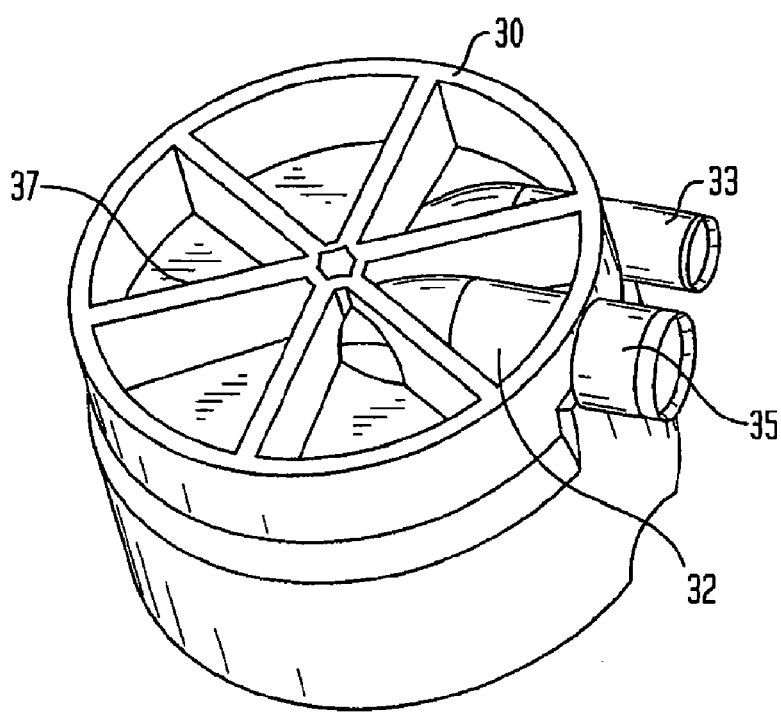
FIG. 6 depicts a filter-housing cap for hemofiltration, the cap being made of flexible PVC and having ribs for stability.

FIG. 5 depicts housing 10 inserted within cap 30. Headspace 31 communicates with outlet 32, which in turn communicates with bond socket 35. Headspace 31 ranges from approximately 1.5 mm at the outer edge to approximately 3 mm in the center of the dome-like region. In use, the pressure in headspace 31 can reach 40 PSI (2000 mmHg), resulting in 25 lbs force pushing the cap off. The cap 30 may therefore need to be bonded, threaded, or snapped on, or attached by other suitable means, to withstand pressure. Solvent bonding and use of a threaded cap are two suitable means to accomplish attachment. It will again be understood that these device dimension are merely illustrative as stated above. FIG. 6 depicts a top view of another embodiment of cap 30 having ribs 37.

Although the foregoing invention has, for the purposes of clarity and understanding, been described in some detail by way of illustration and example, it will be obvious that certain changes and modifications may be practiced which will still fall within the scope of the appended claims. For example, it will be understood that any feature of any device or method disclosed herein can be used with any of the other devices or methods, even though any given figure might depict only a particular combination.

What is claimed is:

1. A method for filtering blood, comprising:
   providing an extracorporeal blood filter, the filter comprising a housing having an interior volume separated by filter media into a non-blood part and blood part; the housing including a cap that defines a headspace, between the filter media and the cap, in fluid communication with the blood part; the cap having a blood port configured for attachment to external tubing for blood supply between the extracorporeal blood filter and an external blood supply line and a dilution fluid port, through which dilution fluid flows, opening directly to the headspace such that these ports are connected only through the headspace; and at least one port connected to the non-blood part;
   flowing blood through the blood part while simultaneously flowing blood in the headspace, flowing blood through the blood port, and flowing dilution fluid through the dilution fluid port into the headspace, such that dilution fluid is mixed with blood in the headspace.

2. The method of claim 1, wherein the flowing blood in the headspace includes flowing blood from the blood port into the headspace and the flowing dilution fluid in the headspace is effective to predilute blood passing into the blood part.

3. The method of claim 1, wherein the flowing the flowing blood in the headspace includes flowing blood from the blood part into the headspace and the flowing dilution fluid in the headspace is effective to post-dilute blood passing from the blood part.

4. The method of claim 1, wherein the flowing dilution fluid is at such a velocity and direction that swirling of the blood and dilution fluid occurs in the headspace.

5. The method of claim 1, wherein the headspace is circular and the flowing dilution fluid includes directing dilution fluid in a tangential flow path in the headspace.

6. The method of claim 1, wherein the blood flowing in the headspace is thoroughly mixed with the dilution fluid in the headspace.

7. The method of claim 1, the flowing dilution fluid includes sweeping particles of thrombus in the headspace.

8. The method of claim 1, wherein the dilution fluid is a physiological fluid containing at least one of saline and lactate.

9. The method of claim 1, wherein the filter media includes filter fibers with ends, the headspace lying between the ends of the filter fibers and the cap.

10. The method of claim 1, wherein the headspace has a depth of not more than 3 mm between the filter media and the cap.

11. The method of claim 1, wherein the headspace has an internal shape and size for minimizing formation of blood clots.

* * * * *